US010426408B2

(12) United States Patent
Nakanishi et al.

(10) Patent No.: US 10,426,408 B2
(45) Date of Patent: Oct. 1, 2019

(54) SIGNAL DETECTION DEVICE AND SIGNAL DETECTION METHOD

(71) Applicant: Panasonic Intellectual Property Management Co., Ltd., Osaka (JP)

(72) Inventors: Masahiro Nakanishi, Kyoto (JP); Yoshifumi Hirose, Kyoto (JP); Shoichi Araki, Osaka (JP)

(73) Assignee: Panasonic Initellectual Property Management Co., Ltd., Osaka (JP)

( * ) Notice: Subject to any disclaimer, the term of this patent is extended or adjusted under 35 U.S.C. 154(b) by 326 days.

(21) Appl. No.: 15/434,582

(22) Filed: Feb. 16, 2017

(65) Prior Publication Data
US 2017/0156677 A1 Jun. 8, 2017

Related U.S. Application Data

(63) Continuation of application No. PCT/JP2016/003695, filed on Aug. 10, 2016.

(30) Foreign Application Priority Data

Aug. 26, 2015 (JP) .................................. 2015-166939

(51) Int. Cl.
*A61B 5/00* (2006.01)
*A61B 5/0404* (2006.01)
(Continued)

(52) U.S. Cl.
CPC .......... *A61B 5/7225* (2013.01); *A61B 5/0245* (2013.01); *A61B 5/02438* (2013.01);
(Continued)

(58) Field of Classification Search
CPC . A61B 5/7225; A61B 5/7203; A61B 5/02438; A61B 5/0245; A61B 5/0452;
(Continued)

(56) References Cited

U.S. PATENT DOCUMENTS 3,872,455 A * 3/1975 Fuller .................. A61B 5/0002
340/870.05
5,704,365 A * 1/1998 Albrecht .............. A61B 5/0408
128/901
(Continued)

FOREIGN PATENT DOCUMENTS

JP H01-115344 A 5/1989
JP 2000-194400 A 7/2000
(Continued)

OTHER PUBLICATIONS

Hamann , Investigation of pattern generating mechanisms during atrial fibrillation based on the FitzHugh Nagumo equations (Year: 2008).*

(Continued)

*Primary Examiner* — Stephanie E Bloss
*Assistant Examiner* — Mohammad K Islam
(74) *Attorney, Agent, or Firm* — McDermott Will & Emery LLP

(57) ABSTRACT

A signal detection device includes a measurer, an arithmetic operation unit, and signal period detector, and detects information such as a cardiac cycle with high accuracy by causing resonance of only a signal such as a heartbeat, the signal having strong pulse characteristics. The measurer measures a signal. The arithmetic operation unit performs nonlinear arithmetic operation processing for amplifying a pulse-like component of the signal measured by the measurer and suppressing a component other than the pulse-like component of the signal measured by the measurer. The signal period detector detects a periodic signal from an output of the arithmetic operation unit.

19 Claims, 17 Drawing Sheets

(51) Int. Cl.
*A61B 5/04* (2006.01)
*A61B 5/024* (2006.01)
*A61B 5/0245* (2006.01)
*A61B 5/0452* (2006.01)

(52) U.S. Cl.
CPC .......... *A61B 5/0452* (2013.01); *A61B 5/7203* (2013.01); *A61B 5/04002* (2013.01); *A61B 5/0404* (2013.01); *A61B 5/6804* (2013.01); *A61B 5/6833* (2013.01)

(58) Field of Classification Search
CPC ... A61B 5/6804; A61B 5/6833; A61B 5/0404; A61B 5/04002
See application file for complete search history.

(56) References Cited

U.S. PATENT DOCUMENTS

| | | | | |
|---|---|---|---|---|
| 5,709,214 | A * | 1/1998 | Skinner | A61B 5/0464 600/300 |
| 5,738,104 | A * | 4/1998 | Lo | A61B 5/02438 600/509 |
| 6,502,067 | B1 | 12/2002 | Hegger et al. | |
| 2005/0124848 | A1 | 6/2005 | Holzner | |
| 2009/0082681 | A1* | 3/2009 | Yokoyama | A61B 5/024 600/509 |
| 2010/0211404 | A1* | 8/2010 | Skinner | A61B 5/04012 705/2 |
| 2011/0066042 | A1* | 3/2011 | Pandia | A61B 5/029 600/484 |
| 2011/0125060 | A1* | 5/2011 | Telfort | A61B 7/003 600/586 |
| 2012/0022844 | A1* | 1/2012 | Teixeira | A61B 5/0205 703/11 |
| 2012/0065536 | A1* | 3/2012 | Causevic | A61B 5/04004 600/544 |
| 2012/0123232 | A1* | 5/2012 | Najarian | A61B 5/0022 600/345 |
| 2013/0066395 | A1* | 3/2013 | Simon | A61N 2/006 607/48 |
| 2013/0088294 | A1* | 4/2013 | Heineman | H03F 1/26 330/207 A |
| 2013/0237874 | A1* | 9/2013 | Zoicas | A61B 5/0452 600/521 |
| 2014/0163386 | A1* | 6/2014 | He | A61B 5/7203 600/476 |
| 2015/0046095 | A1* | 2/2015 | Takahashi | A61B 5/02416 702/19 |
| 2015/0065896 | A1* | 3/2015 | Takahashi | A61B 5/721 600/500 |
| 2015/0088013 | A1* | 3/2015 | Nakamura | A61B 5/721 600/500 |
| 2015/0342490 | A1* | 12/2015 | Sachin | A61B 5/686 600/521 |
| 2016/0106332 | A1* | 4/2016 | Takeshima | A61B 5/0452 600/521 |
| 2016/0192853 | A1* | 7/2016 | Bardy | A61B 5/7203 600/382 |
| 2017/0079596 | A1* | 3/2017 | Teixeira | G06K 9/00496 |

FOREIGN PATENT DOCUMENTS

| | | |
|---|---|---|
| JP | 2002-024794 A | 1/2002 |
| JP | 2002-221546 A | 8/2002 |
| JP | 2014-094043 A | 5/2014 |
| JP | 2015-097638 A | 5/2015 |

OTHER PUBLICATIONS

Berenfeld et al., Simulation of cardiac activity and the ECG using a heart model with a reaction-diffusion action potential (Year: 1996).*

Paton et al., A study of wave propagation in the FitzHugh Nagumo system (Year: 2008).*

Qu et al., Nonlinear and stochastic dynamics in the heart. (Year: 2014).*

International Search Report issued in Application No. PCT/JP2016/003695 dated Nov. 1, 2016.

* cited by examiner

SIGNAL DETECTION DEVICE AND SIGNAL DETECTION METHOD

RELATED APPLICATIONS

This application is a continuation of International Application No. PCT/JP2016/003695, filed on Aug. 10, 2016, which in turn claims the benefit of Japanese Application N. 2015-166939, filed on Aug. 26, 2015, the disclosures of which are incorporated by reference herein.

BACKGROUND

1. Technical Field

The present disclosure relates to a signal detection device and a signal detection method, which detect a weak periodic signal by using a nonlinear oscillator.

2. Description of Related Art

A conventional signal detection device includes a measurer that senses a heartbeat and the like, an arithmetic operation unit that performs filtering for suppressing noise, and a signal period detector. For example, the measurer is a clothes-type sensor in which electrodes embedded in a shirt. The measurer sometimes senses a heartbeat obtained while a subject is doing exercise such as body side flexion. In such a case, with regard to the measurer, since a contact impedance thereof with a surface of a body of the subject is prone to vary, detection accuracy thereof for the heartbeat is degraded.

SUMMARY

A signal detection device of the present disclosure includes a measurer, an arithmetic operation unit, and a signal period detector. The measurer measures a signal. The arithmetic operation unit performs nonlinear arithmetic operation processing for amplifying a pulse-like component of the signal measured by the measurer and suppressing a component other than the pulse-like component of the signal measured by the measurer. The signal period detector detects a periodic signal from an output of the arithmetic operation unit.

In accordance with the signal detection device and the signal detection method of the present disclosure, even in a case where an impedance between the signal detection device and a surface of a body fluctuates due to exercise such as body side flexion, a pulse-like signal such as a heartbeat waveform can be detected with high accuracy.

DETAILED DESCRIPTION

Hereinafter, exemplary embodiments will be described in detail with appropriate reference to the drawings. However, a description more in detail than necessary is omitted in some case. For example, a detailed description of a well-known item and a duplicate description of the same configuration are omitted in some case. These omissions are made in order to avoid unnecessary redundancy of the following description and to facilitate the understanding of those skilled in the art.

Note that the accompanying drawings and the following description are provided in order to allow those skilled in the art to fully understand this disclosure, and it is not intended to thereby limit the subject of the description of the scope of claims.

(First Exemplary Embodiment)

Figure 1:
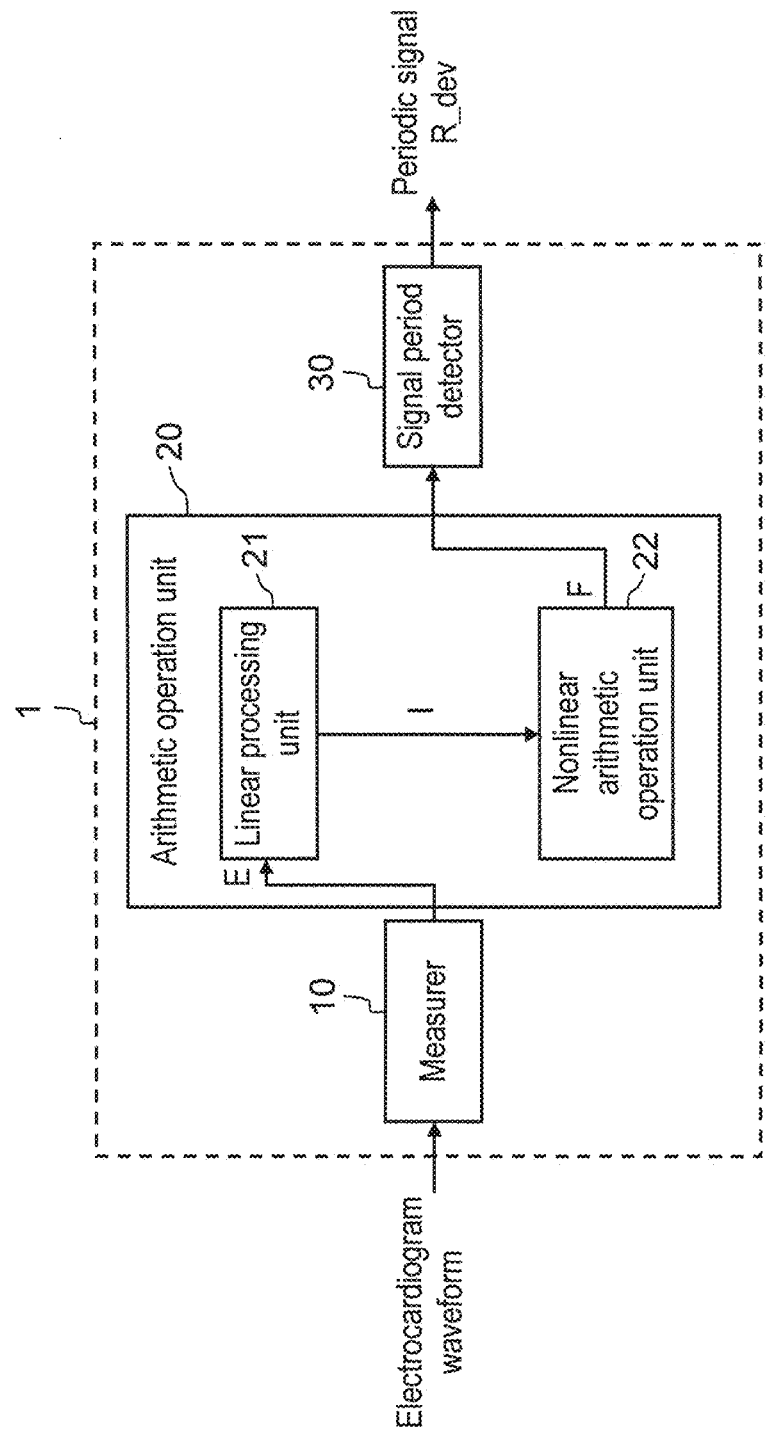
FIG. 1 is a block diagram showing a configuration of a signal detection device in a first exemplary embodiment.

FIG. 1 is a block diagram showing a configuration of signal detection device 1 according to a first exemplary embodiment. Signal detection device 1 includes measurer 10, arithmetic operation unit 20, and signal period detector 30.

Measurer 10 is a device that detects (senses) an electrocardiogram waveform. For example, measurer 10 is a device using a patch that adheres to a surface of a body in a vicinity of a heart, a device embedded in clothes such as a T-shirt, a device embedded in a band wrapped around a breast or an arm, or the like. Then, measurer 10 detects an electrocardiogram waveform from the surface of the body.

Arithmetic operation unit 20 includes linear processing unit 21 and nonlinear arithmetic operation unit 22. Linear processing unit 21 performs filtering in order to suppress noise of the electrocardiogram waveform detected by measurer 10. By the filtering, linear processing unit 21 suppresses a low frequency component of the electrocardiogram waveform detected by measurer 10. Nonlinear arithmetic operation unit 22 arithmetically operates the electrocardiogram waveform, which is subjected to the filtering in linear processing unit 21, by an operation of a nonlinear oscillator, which is written by a nonlinear simultaneous differential equation of Expression 2. In this way, nonlinear arithmetic operation unit 22 performs nonlinear arithmetic operation processing for amplifying a pulse-like component in a signal measured by measurer 10, and suppressing a component other than the pulse-like component of the signal. Note that, for the operation of the nonlinear oscillator, an FN (FitzHugh-Nagumo) equation of a mathematical model showing a behavior of myocardial cells, nerve cells or the like. The FN equation is shown in Expression 1.

[Expression 1]

$$\frac{dv}{dt} = c\left(-w + v - \frac{v^3}{3} + in\right) \quad (1a)$$

$$\frac{dw}{dt} = v - bw + a \quad (1b)$$

where IN is an input to nonlinear arithmetic operation unit 22, and v is an output of nonlinear arithmetic operation unit 22, and is a variable corresponding to a membrane potential of each of the cells. w is a variable for obtaining dv/dt. a, b, and c are constants, for which typical values are used. a, b, and c are set equal to 0.7, 0.8, 10.0, respectively (a=0.7, b=0.8, c=10.0).

Moreover, in order to arithmetically operate a behavior of the FN equation shown in Expression 1, nonlinear arithmetic operation unit 22 derives a difference equation of Expression 2 in which the Euler method is applied to Expression 1.

[Expression 2]

$$v_n dot = c\left(-w_n + v_n - \frac{v_n^3}{3} + in\right) \quad (2a)$$

$$w_n dot = v_n - bw_n + a \quad (2b)$$

$$v_{n+1} = v_n + v_n dot \cdot \Delta T \quad (2c)$$

$$w_{n+1} = w_n + w_n dot \cdot \Delta T \quad (2d)$$

where IN is an input to the nonlinear arithmetic operation unit, $v_n$ is an output of the nonlinear arithmetic operation unit, and $w_n$ is a variable for obtaining $v_n$dot. $v_n$dot is a first derivative of $v_n$. $w_n$dot is a first derivative of $w_n$. $\Delta T$ (delta T) indicates a time difference term.

Moreover, as an arithmetic operation condition, a sampling frequency Fs is set equal to 200 (Hz) (Fs=200 (Hz)), the time difference term $\Delta T$ is set equal to 0.05 ($\Delta T$=0.05), $v_0$ is set equal to 0 ($v_0$=0), and $w_0$ is set equal to 0 ($w_0$=0).

Figure 11:
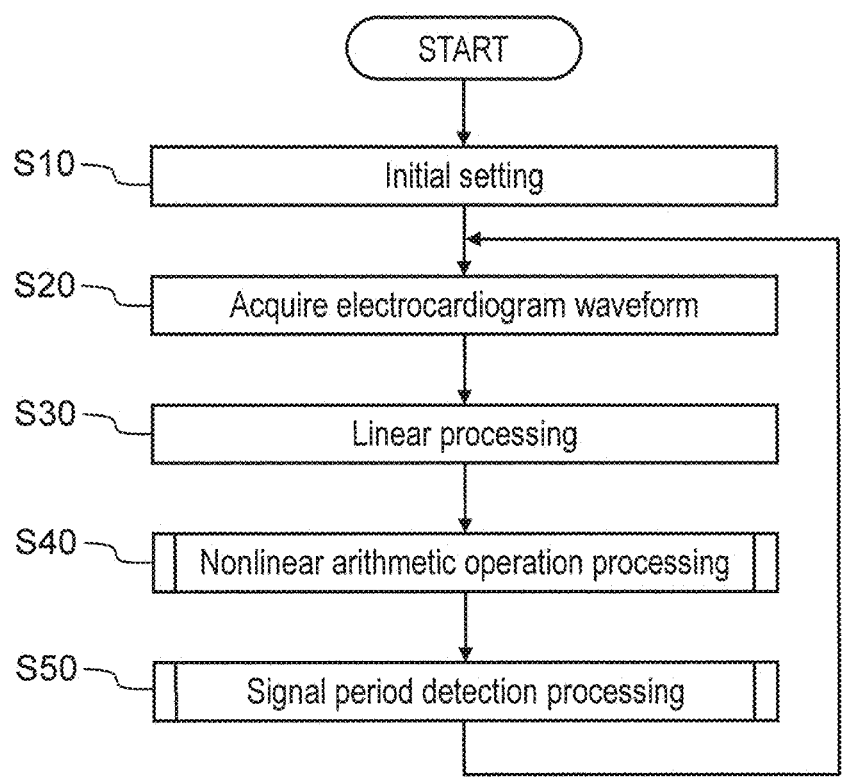
FIG. 11 is a flowchart of processing by the signal detection device in the first exemplary embodiment.
Figure 12:
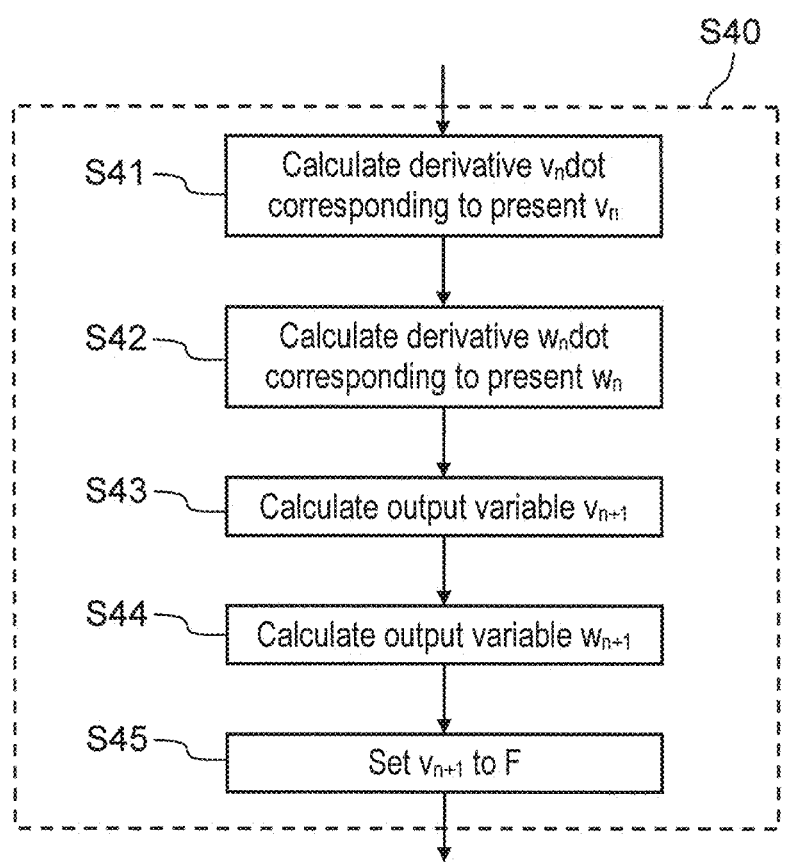
FIG. 12 is a flowchart of processing by a nonlinear arithmetic operation unit in the first exemplary embodiment.
Figure 13:
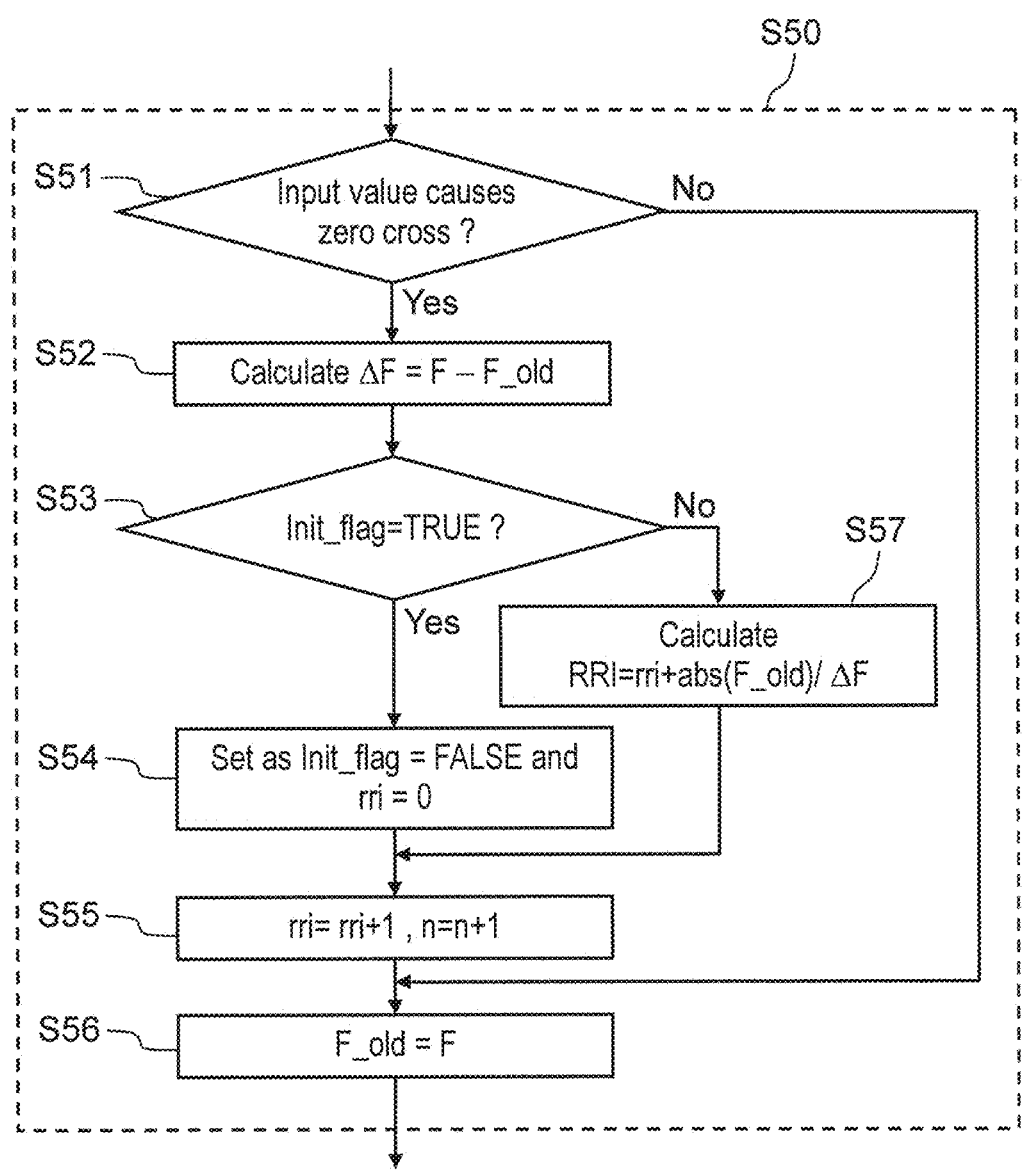
FIG. 13 is a flowchart of processing by a signal period detector in the first exemplary embodiment.

Signal period detector 30 detects a periodic signal R_dev from an output signal F of arithmetic operation unit 20 in accordance with flowcharts shown in FIG. 11 to FIG. 13. Note that arithmetic operation unit 20 and signal period detector 30 may be those realized by programs by using a CPU and a DSP (Digital Signal Processor). Moreover, arithmetic operation unit 20 and signal period detector 30 may be those realized by hardware such as an electronic circuit and an LSI. The flowcharts of FIG. 11 to FIG. 13 will be described later.

Figure 2:
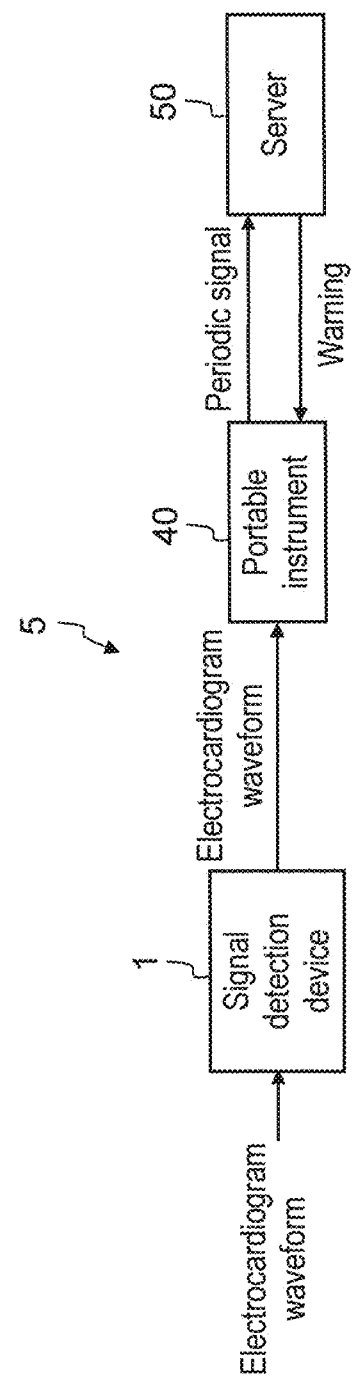
FIG. 2 is a block diagram of a health care system in the first exemplary embodiment.

FIG. 2 is a block diagram of health care system 5 using signal detection device 1. A cardiac cycle that is the periodic signal detected by signal detection device 1 is transferred to server 50 via portable instrument 40 such as a smart phone. Based on a time variation of the cardiac cycle and the like, server 50 estimates a stress and wakefulness level, and notifies a user of a warning via portable instrument 40.

Next, a description will be made of an output variable v which nonlinear arithmetic operation unit 22 using the difference equation of Expression 2 outputs in "a case of having received a step signal" and "a case of having received the periodic signal".

[Output in Case of Having Received Step Signal]

Figure 3:
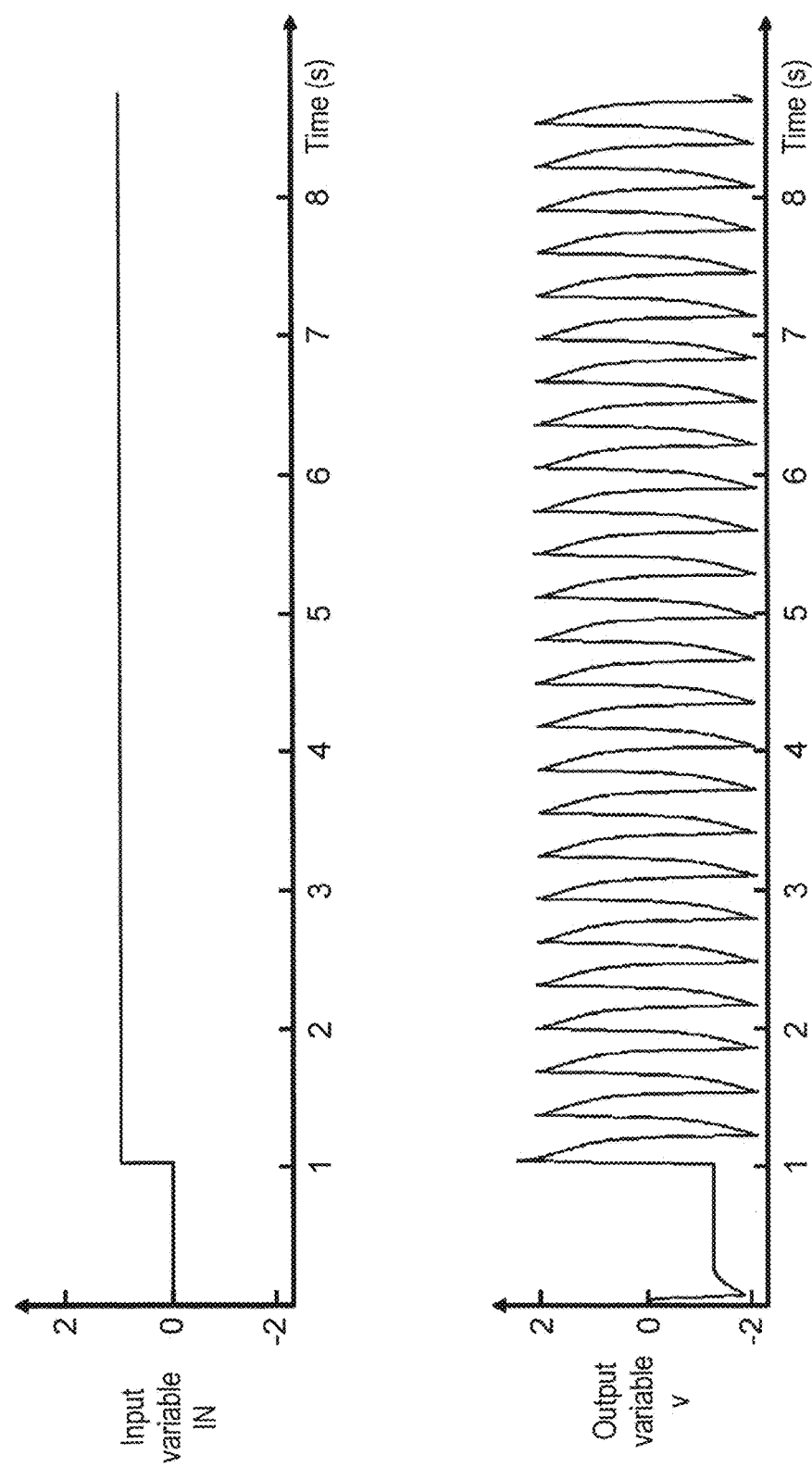
FIG. 3 is graphs in a case of inputting a step signal to an arithmetic operation unit of the first exemplary embodiment.

A description will be made of the output variable v as a signal which nonlinear arithmetic operation unit 22 outputs at a time of having received the step signal as an input variable IN of nonlinear arithmetic operation unit 22 as shown in FIG. 3. When the input variable IN is 0 (a time 0 s to 1 s), the output variable v holds a constant value between −1 to −2. When the input variable IN is 1 (from the time 1 s), the output variable v turns to a self-oscillation state. Note that, when the input variable IN stays within an approximate range of 0.33 to 1.42, the output variable v turns to the self-oscillation. When the input variable IN goes out of the above-described range, the output variable v does not cause the self-oscillation. Moreover, as an input level is higher, a frequency of the self-oscillation becomes higher.

[Output in Case of Applying Periodic Signal]

Figure 4:
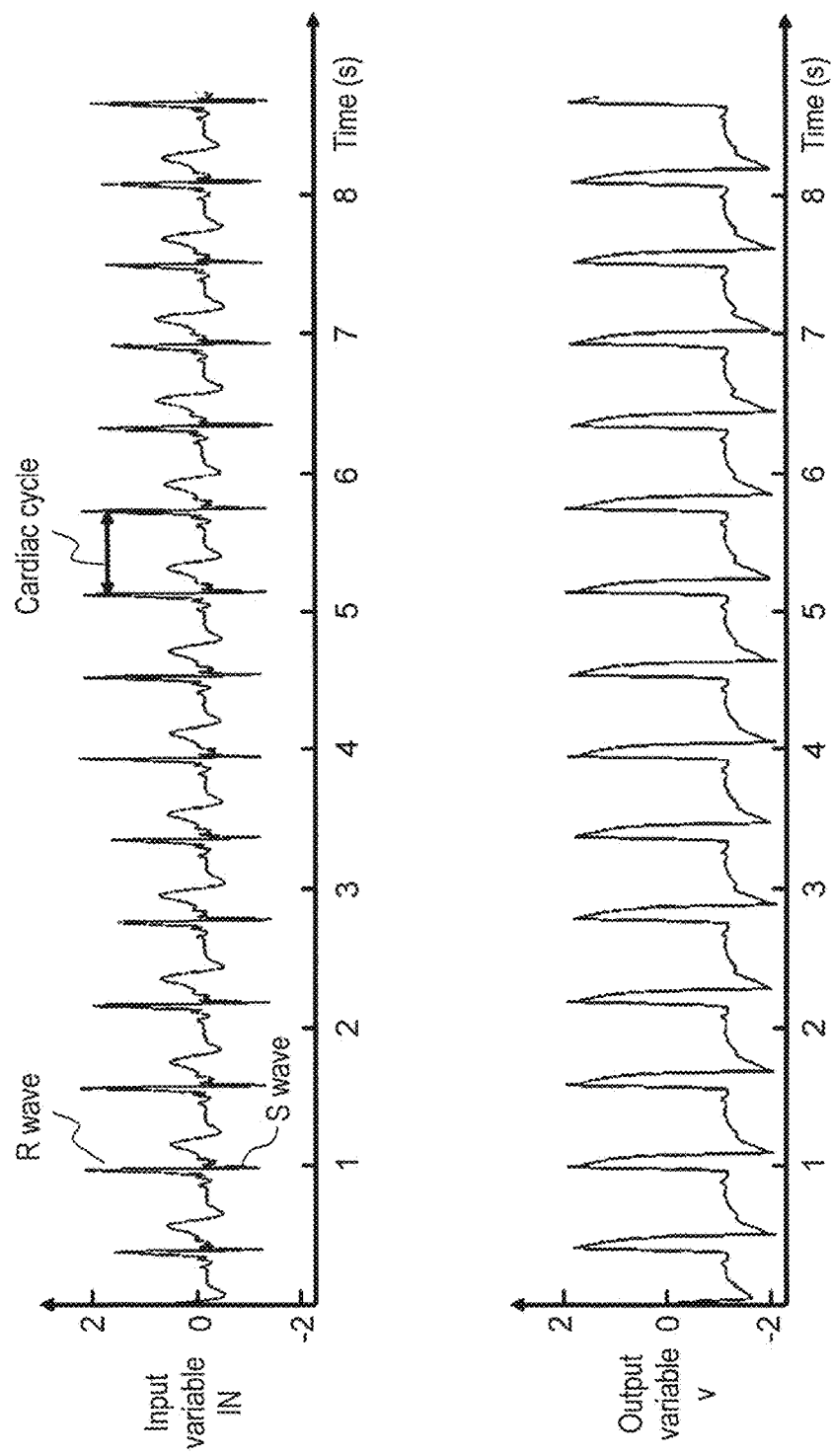
FIG. 4 is graphs in a case of inputting a heartbeat signal at a walking time to the arithmetic operation unit, of the first exemplary embodiment.

Meanwhile, a description will be made of the output variable v of nonlinear arithmetic operation unit 22 at a time when the input variable IN of nonlinear arithmetic operation unit 22 is the periodic signal as shown in FIG. 4. The periodic signal shown in the input variable IN of FIG. 4 is an electrocardiogram waveform measured when a subject starts to walk at a 5 km/h. In this case of measuring the electrocardiogram waveform, a clothes-type sensor in which electrodes are embedded in a shirt is used. In the output variable v, a positive portion of a sharp pulse component is referred to as an R wave, and a negative portion of the sharp pulse component is referred to as an S wave. In general, a time interval between such R waves adjacent to each other is referred to as the cardiac cycle, and it is recognized that the output variable v alternates in synchronization with this cycle. A phenomenon that the nonlinear oscillator behaves in synchronization with a perturbation wave from the outside as described above is referred to as forced synchronization.

Next, a behavior of nonlinear arithmetic operation unit 22 is investigated. As a result, it is found out that nonlinear arithmetic operation unit 22 has "pulse-sensitivity" and "pulse-synchronization". A description will be made below of "pulse-sensitivity" and "pulse-synchronization".

[Pulse-Sensitivity]

Figure 5:
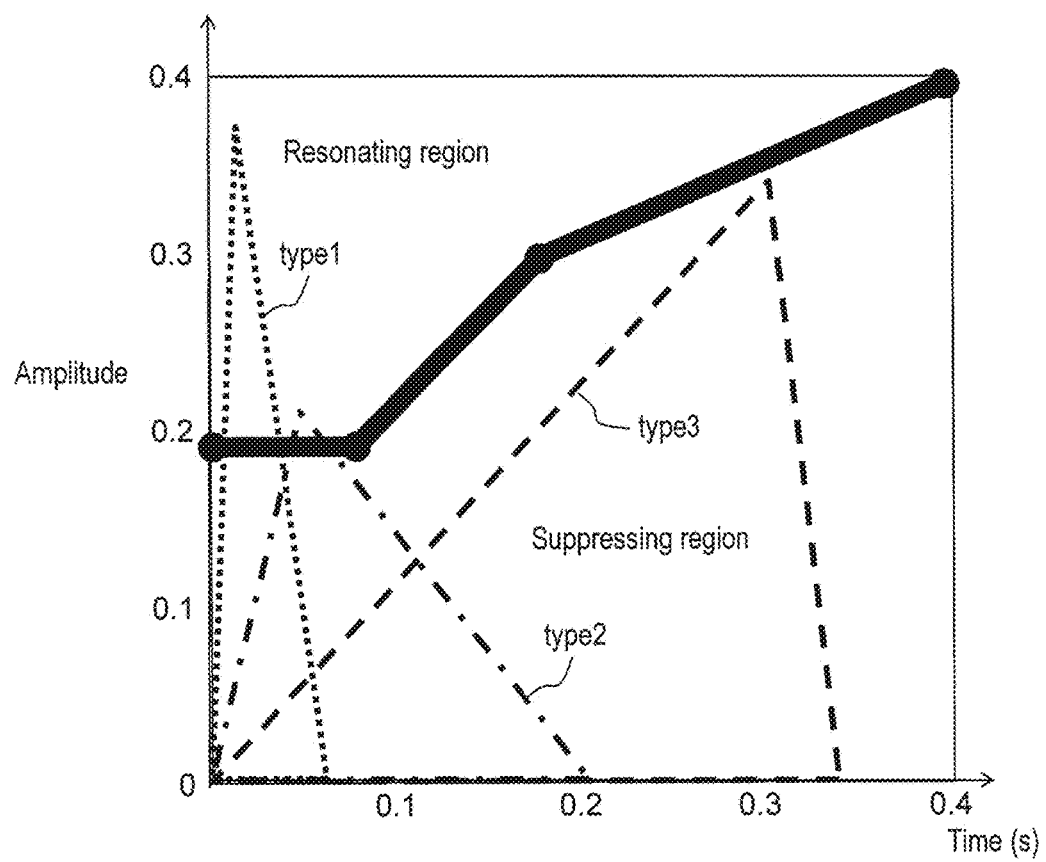
FIG. 5 is a graph showing a condition for resonance in the arithmetic operation unit of the first exemplary embodiment.

FIG. 5 is a graph showing a condition for resonance of nonlinear arithmetic operation unit 22. A time is taken on an axis of abscissa, and an amplitude of the input variable IN is taken on an axis of ordinate. An ascending bold line on a center portion of the graph is a boundary line between a resonating region and a suppressing region. Then, an upper side of the boundary line is the resonating region, and a lower side of the boundary line is the suppressing region.

A repeating waveform (triangular pulse sequence) formed by connecting pulses to one another at a time interval of 600 ms is defined as a representative waveform. Here, each of the pulses is selected from any one of triangles of types 1 to 3 shown in FIG. 5. There was investigated the output variable v of nonlinear arithmetic operation unit 22 when each of such repeating waveforms is given to the input variable IN of nonlinear arithmetic operation unit 22. The repeating waveforms of type 1 and type 2 have apexes in the resonating region in FIG. 5, and nonlinear arithmetic operation unit 22 causes resonance effect on the repeating waveforms. Meanwhile, the repeating waveform of type 3 has an apex in the suppressing region, and nonlinear arithmetic operation unit 22 causes suppression effect on the repeating waveforms.

Figure 6:
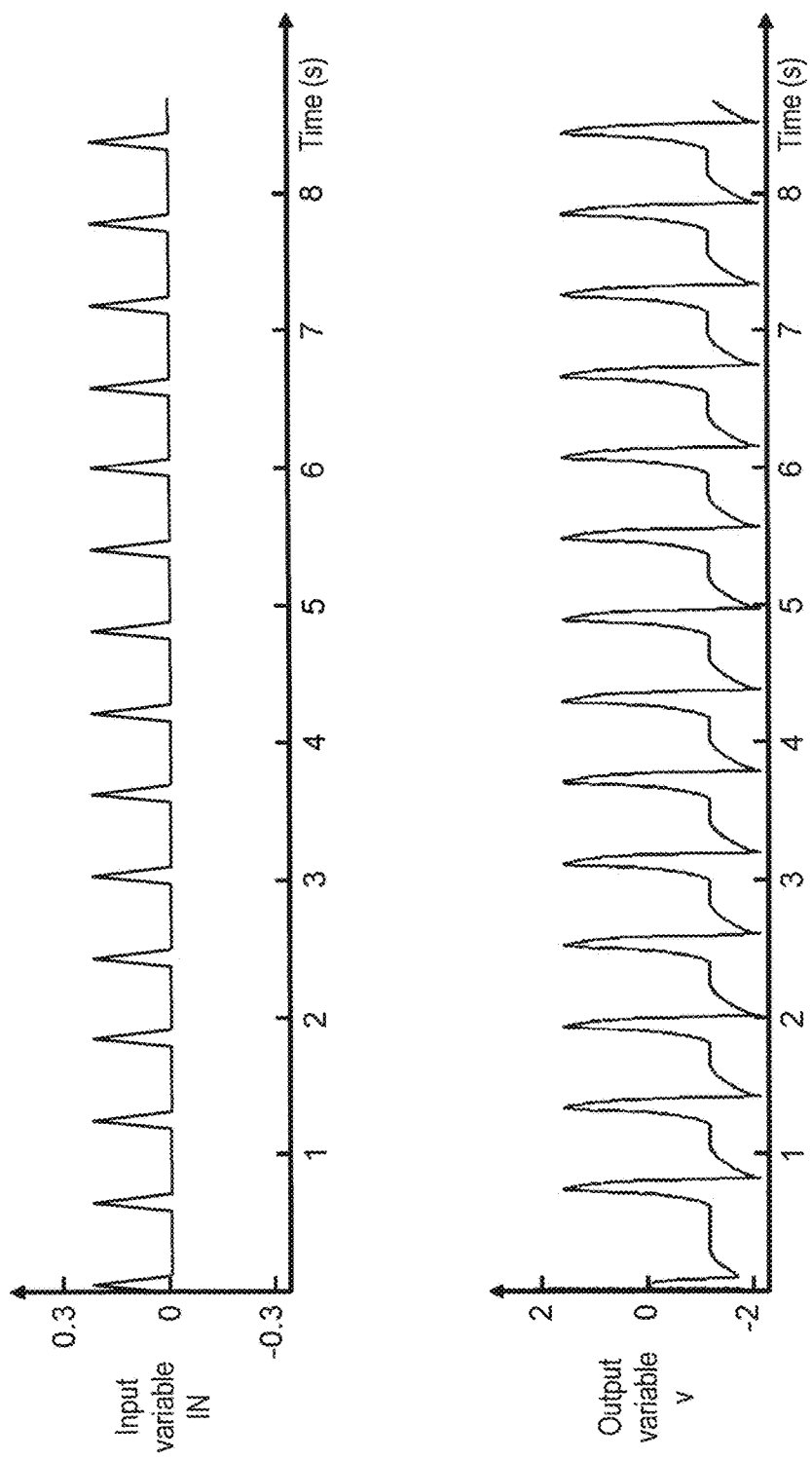
FIG. 6 is graphs in a case of inputting a type 2 repeating waveform to the arithmetic operation unit of the first exemplary embodiment.
Figure 7:
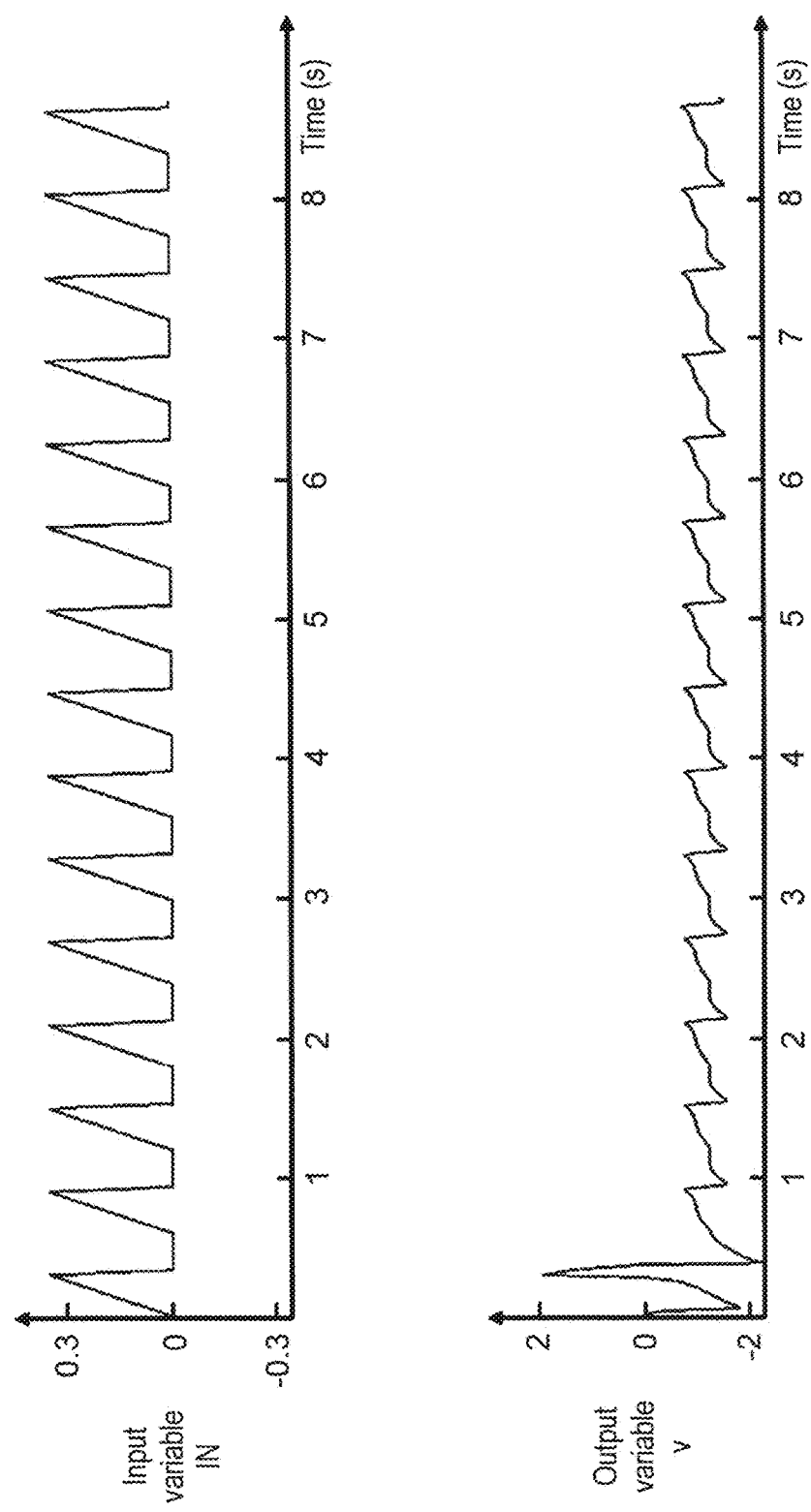
FIG. 7 is graphs in a case of inputting a type 3 repeating waveform to the arithmetic operation unit of the first exemplary embodiment.

FIG. 6 shows a behavior of nonlinear arithmetic operation unit 22, which corresponds to the repeating waveform of type 2. FIG. 7 shows a behavior of nonlinear arithmetic operation unit 22, which corresponds to the repeating waveform of type 3. As shown in FIG. 6, the repeating waveform of type 2 has an apex of the waveform in the resonating region, and accordingly, an output variable v subjected to the resonance effect is obtained. As shown in FIG. 7, output variable v is suppressed where input variable IN is the repeating waveform of type 3, which has an apex in the suppressing region, even though amplitude of repeating waveform of type 3 is larger than that of type 2.

Figure 8:
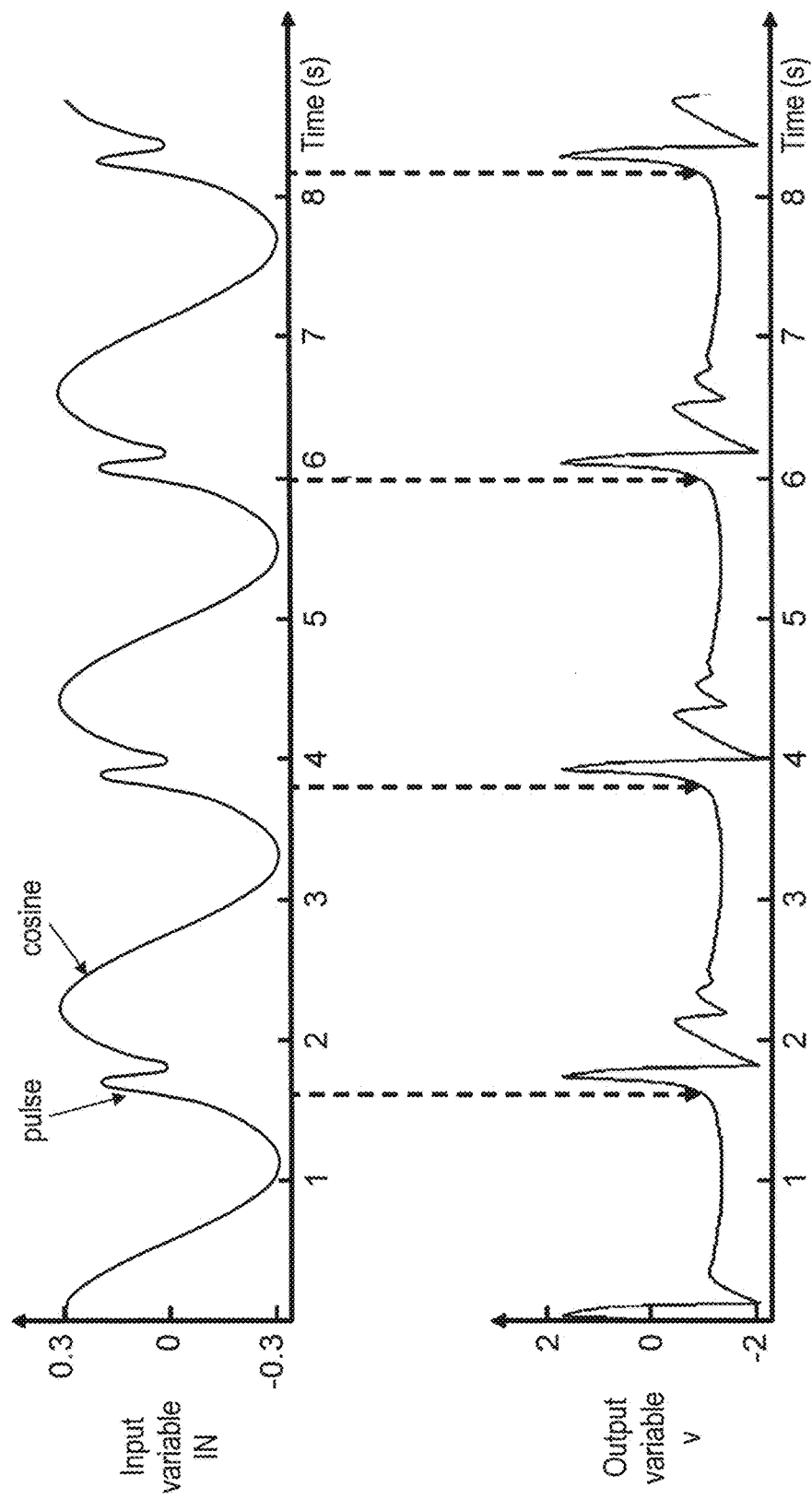
FIG. 8 is graphs in a case of inputting a synthetic waveform of a pulse and a cosine wave to the arithmetic operation unit of the first exemplary embodiment.

FIG. 8 shows a resonance behavior of a repeating waveform which is a superimposed waveform of a pulse waveform, which has the apex in the resonating region, and a cosine wave, which does not have the apex in the resonating region. As shown by arrows of dotted lines, it is understood that, though a peak level of the cosine wave is larger than that of the pulse, only the pulse is affected by the resonance effect.

The resonating region, shown in FIG. 5, has a shape of an inverted triangle, and accordingly, such a waveform having a sharp rise edge is prone to cause a resonance though a peak level thereof is small. Meanwhile, a waveform having a slow rise edge tends to be suppressed though a peak level thereof is large. That is to say, nonlinear arithmetic operation unit 22 has characteristics including the pulse-sensitivity, and accordingly, is effective for period detection of a signal such as a heartbeat, the signal having strong pulse characteristics.

[Stable Amplification]

Figure 9:
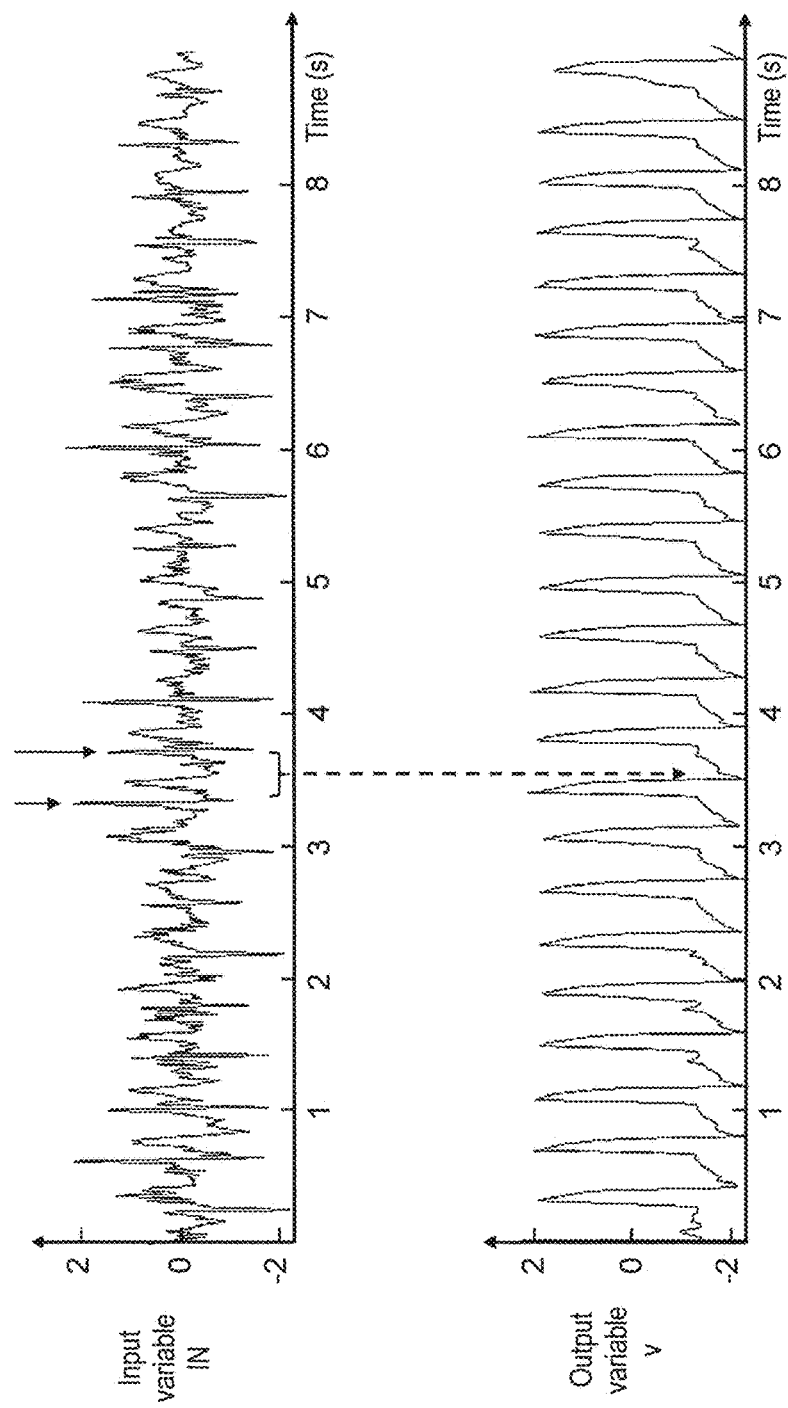
FIG. 9 is graphs in a case of inputting a heartbeat signal at a running time to the arithmetic operation unit of the first exemplary embodiment.

As a merit of nonlinear arithmetic operation unit 22, a stable amplification can be mentioned in addition to the above-mentioned pulse-sensitivity. An input variable IN of FIG. 9 indicates an electrocardiogram when the subject runs at 14 km/h. By such exercise, impedance between the sensor and the surface of the body fluctuates. It means that a noise, called baseline drift, is superimposed on a heartbeat waveform. However, as shown in FIG. 9, the output variable v is in a state of resonating with the R wave of the heartbeat waveform of the input variable IN. In this way, an amplitude envelope of the output variable v keeps a substantially constant level. Moreover, while the R wave having strong pulse characteristics is amplified, components other than the R wave is suppressed. With reference to FIG. 9, an example will be described. In the input variable IN of FIG. 9, two among pieces of the waveform, which indicate noise components other than the R wave, are shown by solid arrows. As shown in the output variable v of FIG. 9, a response of the output variable v to the above-described two noises is subjected to the suppression effect in a negative region of the output variable v. In this way, an influence, which such noise with a large amplitude gives to the output variable v, is suppressed.

As described above, nonlinear arithmetic operation unit 22 outputs such a stable alternate waveform, and accordingly, period detection based on zero-cross detection can be performed for the output variable v. In accordance with the signal detection method of the present disclosure, as described in "Performance comparison between exemplary embodiment and comparative example", which will be described later, relatively stable period detection can be performed even in a case where the level fluctuation of the input variable IN is large.

[Pulse-Synchronization]

A phenomenon that the nonlinear oscillator behaves in synchronization with a frequency of an external perturbation wave is generally referred to as "frequency pulling". Forced synchronization of nonlinear arithmetic operation unit 22 mentioned above corresponds to this phenomenon. In a case where the FN equation is applied to detection of a heart rate, it is necessary to confirm that the pulse-synchronization occurs within a range of the heart rate. Accordingly, the pulse-synchronization was investigated over the range of the heart rate (20 bpm to 250 bpm) shown in Table 1.

Specifically, it was investigated whether a repeating waveform, which is based on repeating waveform of type 1 shown in FIG. 5, resonates in expected manner. Note that the sampling frequency Fs was set equal to 200 (Hz) (Fs=200 (Hz)), and the above-described investigation was performed for cases where values of the time difference term ($\Delta T$) were 0.04, 0.05, 0.075 and 0.10. Results of the investigation are shown in Table 1. When the triangular pulse sequence was input, a case where an output waveform resonated with all of the triangular pulses was indicated to be good (denoted by a circle symbol ○), and a case where the output waveform did not resonate with at least one of the triangular pulses was indicated to be defective (denoted by a cross symbol x). Note that numerals (n/m) on a right side of x show a state where n pieces of the output waveform resonate with respect to in pieces of input pulses. In 0.075 and 0.10 of the time difference term $\Delta T$, the symbol ○ appeared in all patterns of the heart rate; however, short limit cycles of Fs/2 may appears in such peak portions of the waveform of the output variable v. Accordingly, for example, in a case where the heart rate is estimated to be less than 170, the time difference term $\Delta T$ is set to approximately 0.05, and in a case where the heart rate is estimated to be 170 or more, the time difference term $\Delta T$ is switched to a value larger than 0.05. As described above, the time difference term $\Delta T$ is switched in response to the estimated heart rate. Accordingly, the resonation is sensitive to the R wave irrespective to variation of the period between R waves.

TABLE 1

| Heart rate (bpm) | f (Hz) | $\Delta T$ 0.04 | 0.05 | 0.075 | 0.10 |
|---|---|---|---|---|---|
| 20 | 0.3333 | ○ | ○ | ○ | ○ |
| 40 | 0.6667 | ○ | ○ | ○ | ○ |
| 60 | 1.0000 | ○ | ○ | ○ | ○ |
| 75 | 1.2500 | ○ | ○ | ○ | ○ |
| 100 | 1.6667 | ○ | ○ | ○ | ○ |
| 115 | 1.9167 | ○ | ○ | ○ | ○ |
| 120 | 2.0000 | x (2/3) | ○ | ○ | ○ |
| 150 | 2.5000 | x | ○ | ○ | ○ |
| 165 | 2.7500 | x | ○ | ○ | ○ |
| 170 | 2.8333 | x | x (4/5) | ○ | ○ |
| 200 | 3.3333 | x | x | ○ | ○ |
| 230 | 3.8333 | x | x | ○ | ○ |
| 250 | 4.1667 | x | x | ○ | ○ |

[Regarding Processing from Electrocardiogram Waveform Measurement to Period Detection]

Figure 10:
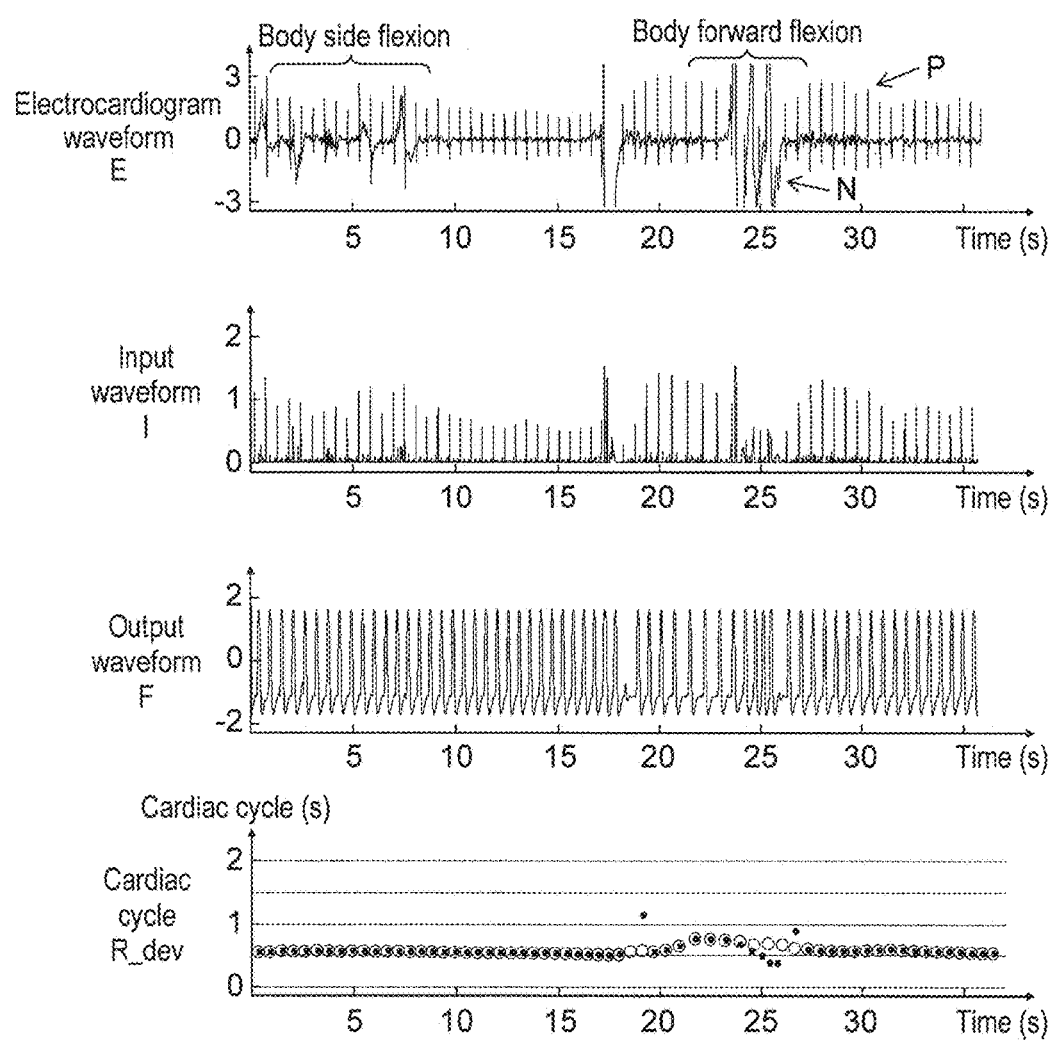
FIG. 10 is graphs showing a variety of signals in a periodic signal detection operation of the signal detection device in the first exemplary embodiment.

FIG. 10 shows waveforms of a variety of signals in a periodic signal detection operation of the signal detection device. Specifically, FIG. 10 shows relationships among an electrocardiogram waveform E, an input waveform I, an output waveform F and the cardiac cycle R_dev. The electrocardiogram waveform E is a waveform measured by measurer 10. Linear processing unit 21 receives the electrocardiogram waveform E, and outputs the input waveform I to nonlinear arithmetic operation unit 22. The input waveform I is a time waveform of a pulse sequence obtained by filtering the electrocardiogram waveform E by linear processing unit 21. Nonlinear arithmetic operation unit 22 receives the input waveform I, and outputs the output waveform F to signal period detector 30. The output waveform F is a time waveform of the resonating signal subjected to the arithmetic operation processing by nonlinear arithmetic operation unit 22. Signal period detector 30 receives the output waveform F, and outputs the cardiac cycle (periodic signal) R_dev. The cardiac cycle R_dev is a cycle obtained by detecting a heartbeat based on the output waveform F.

The electrocardiogram waveform E is an electrocardiogram waveform measured from the surface of the body by measurer 10 when the subject puts on the clothes-type sensor and does body side flexion and forward flexion. As shown in FIG. 10, baseline drift noise N is generated to a large extent during a period while the subject does these exercises.

The input waveform I is such a time waveform I of the pulse sequence generated by the filtering for the received electrocardiogram waveform E, the filtering being performed by linear processing unit 21. This linear processing includes: low-frequency cutoff filtering for cutting a low-frequency component including a DC component; and high-frequency cutoff filtering for cutting high-frequency noise. Moreover, the linear processing includes such processing for obtaining an absolute value of the pulse so that the pulse can stay within a positive region in order that signal period detector 30 can detect the pulse with ease. The input waveform I is a waveform obtained by filtering the electrocardiogram waveform E by the linear processing of linear processing unit 21. Amplitude of the input waveform I is disturbed when the noise N is mixed into the electrocardiogram waveform E.

The output waveform F is a waveform generated by resonance processing of the EN equation by nonlinear arithmetic operation unit 22 using the received input waveform I.

The cardiac cycle R_dev is a graph showing a time interval between points where the resonating signal F and an axis of coordinates of amplitude 0 intersect (zero-cross) each other, that is, showing the periodic signal. Even in a period while the baseline drift noise N is generated in the electrocardiogram waveform E, signal period detector 30 can almost detect the cardiac cycle. Note that, in the cardiac cycle R_dev of FIG. 10, the cardiac cycle of the electrocardiogram waveform E is indicated by blank circles. Moreover, the cardiac cycle detected by signal period detector 30 is indicated by solid circles. A specific counting method of this time interval will be described next.

The processing from the electrocardiogram waveform measurement to the period detection will be described using the waveforms of FIG. 10 and a flow of the signal detection processing of FIG. 11. First, signal detection device 1 performs initial setting (S10). The initial setting is processing for setting values of the constants a, b and c of nonlinear arithmetic operation u 22 and the time difference term $\Delta T$ thereof to predetermined values, and setting the variables $v_0$ and $w_0$ to 0. In the initial setting, moreover, Init_flag of signal period detector 30 is set to TRUE. Moreover, the variable n for use in nonlinear arithmetic operation unit 22 and signal period detector 30 is set to 0.

Thereafter, measurer 10 measures the electrocardiogram waveform E at a sampling frequency of 200 Hz, and acquires digital data of the electrocardiogram waveform E (S20). An inverse number of the sampling frequency is a sampling period, and measurer 10 executes this Step S20 every sampling period. Linear processing unit 21 performs the linear processing (filtering such as DC removal) for the electrocardiogram waveform E measured by measurer 10, and extracts the input waveform I (S30). Then, by using Expression 2, nonlinear arithmetic operation unit 22 performs the nonlinear arithmetic operation processing for the input waveform I extracted by linear processing unit 21, and calculates the output waveform F that is the time waveform of the resonating signal (S40). Finally, signal period detector 30 detects the cycle of the heartbeat from the output waveform F calculated by nonlinear arithmetic operation unit 22, and outputs the cardiac cycle R_dev (S50). Then, the processing returns to Step S20. The nonlinear arithmetic operation processing and the period detection will be described below in detail.

[Regarding Nonlinear Arithmetic Operation Processing]

The nonlinear arithmetic operation processing (S40) performed in nonlinear arithmetic operation unit 22 will be described in detail by a flowchart of FIG. 12. First, the derivative $v_n$dot corresponding to the present output variable $v_n$ is calculated by Expression 2a (S41). In a similar way, the derivative $w_n$dot corresponding to the present output variable $w_n$ is calculated by Expression 2b (S42). Next, based on the present output variable $v_n$, the derivative $v_n$dot and the time difference term $\Delta T$, a new output variable $v_{n+1}$ is calculated by Expression 2c (S43). Next, based on the present variable $w_n$, the derivative $w_n$dot and the time difference term $\Delta T$, a new variable $w_{n+1}$ is calculated by Expression 2d (S44). The output variable $v_{n+1}$ calculated in Step S43 is set into the output waveform F, which is the time waveform of the resonating signal, and is transferred to signal period detector 30. Note that the variables n, $v_n$ and $w_n$ are set to 0 in the initial setting (S10). Moreover, since the variable n is increased in the signal period detection processing (S50), $v_{n+1}$ and $w_{n+1}$ are assigned to $v_n$ and $w_n$ in the nonlinear arithmetic operation processing for the next sampling.

[Regarding Signal Period Detection Processing]

The signal period detection processing (S50) performed in signal period detector 30 will be described in detail by a flowchart of FIG. 13. Signal period detector 30 detects the time interval between the zero-cross points adjacent to one another, that is, detects the cycle of the heartbeat. Thereafter, signal period detector 30 determines whether or not the output, waveform F, which is the input from nonlinear arithmetic operation unit 22, causes the zero cross. Specifically, it is determined that the zero cross is caused when F_old, which is an immediately previous value of the output waveform F, is negative, and a value of an output waveform F, which is newly input, becomes positive (S51).

In a case where it is determined that the zero cross is not caused in Step S51, then the processing skips to Step S56, where the value of the output waveform F, which is newly input, is held to F_old (S56), and the signal period detection processing (S50) is ended. Then, the processing returns to Step S20. Note that an interval of executing this flow corresponds to the inverse number (sampling period) of the sampling frequency Fs.

In a case where it is determined that the zero cross is caused in Step S51, a variation $\Delta F$, which is a difference between the new value of the output waveform F and the immediately previous value F_old thereof, is calculated (S52). Then, it is determined whether or not Init_flag is TRUE (S53).

In a case where it is determined that Init_flag is TRUE in Step S53, Init_flag is set to FALSE, and in addition, a variable rri is set to 0 (S54). Thereafter, the variable rri is increased (S55). Next, the new value of the output variable F is held to the immediately previous value F_old (S56), and the signal period detection processing (S50) is ended. Then, the processing returns to Step S20.

In a case where it is determined that Init_flag is not TRUE in Step S53, the time interval between the zero-cross points adjacent to each other is obtained. Here, the variable rri is a counter for counting a number of sampling times. A variable RRI corresponds to a number of sampling times from an immediately previous zero-cross point to a newly detected zero-cross point. A product obtained by multiplying the variable RRI by the sampling period corresponds to the time interval between the zero-cross points adjacent to each other. Signal period detector 30 calculates the time interval between the zero-cross points, which are adjacent to each other, as described above, and outputs the calculated time interval as the cycle of the heartbeat, and the processing proceeds to Step S55. Note that the variable RRI is not limited to a natural number, and can take a decimal value by linear interpolation to be described later. A decimal portion of the variable RRI is calculated as $abs(F\_old)/\Delta F$. An integral portion of the variable RRI is the variable rri. The variable RRI can be obtained as $abs(F\_old)/\Delta F+rri$, which is a sum of the decimal portion and the integral portion (S57). This processing is so-called linear interpolation, and by doing this processing, the time interval between the zero-cross points adjacent to each other can be specified with higher accuracy than that of the sampling period.

[Performance Comparison Between Exemplary Embodiment and Comparative Example]

Figure 14:
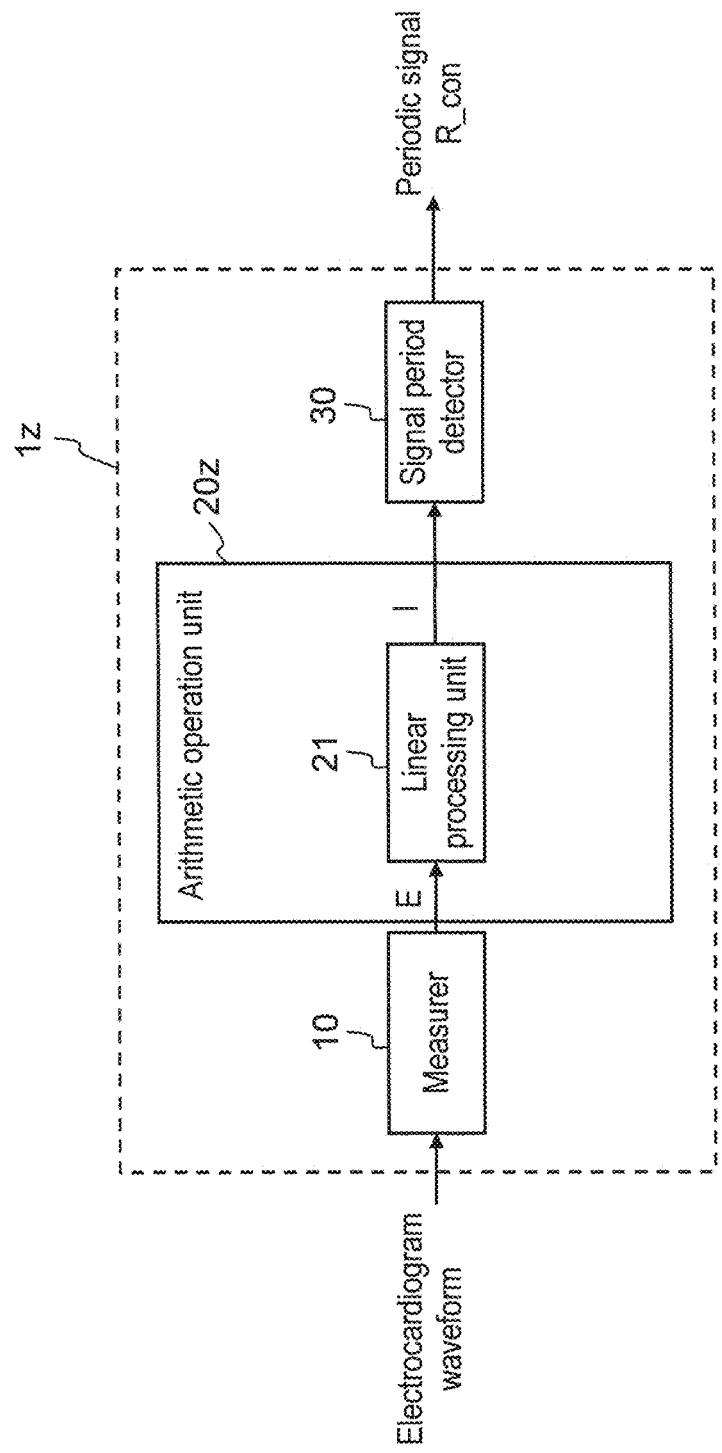
FIG. 14 is a block diagram showing a configuration of a signal detection device in a comparative example.
Figure 15:
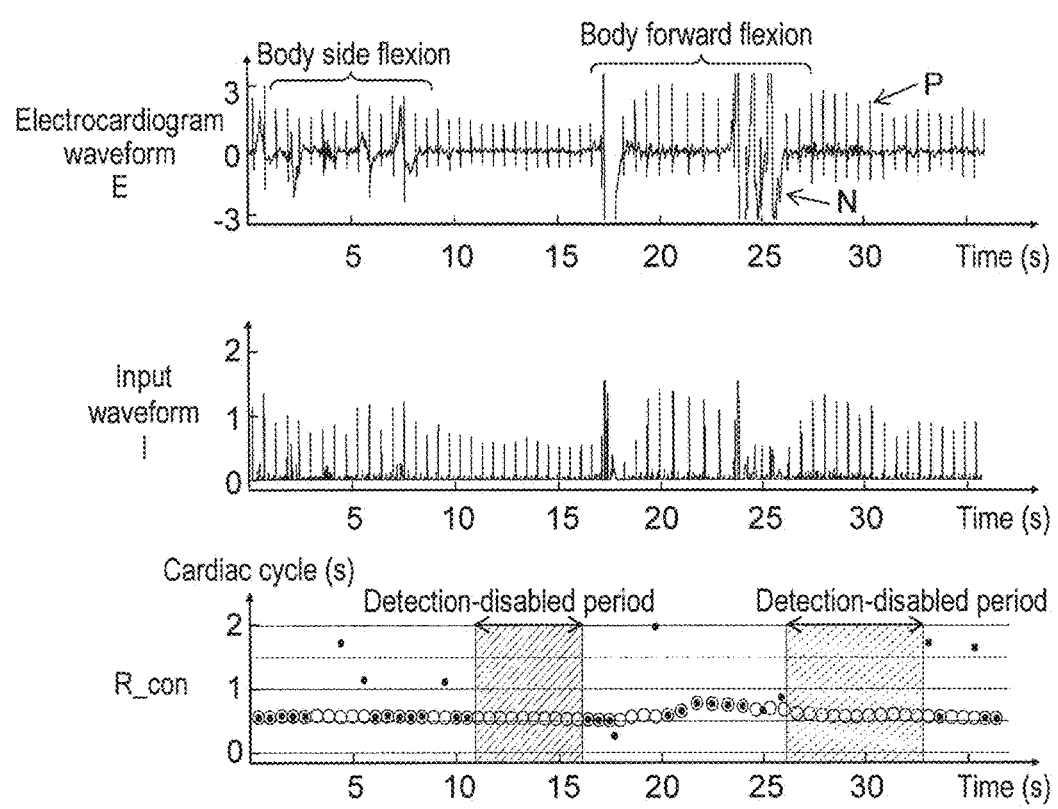
FIG. 15 is graphs showing a variety of signals in a periodic signal detection operation of the signal detection device in the comparative example.

As shown in FIG. 14, signal detection device 1z composed of arithmetic operation unit 20z, which is made of only linear processing unit 21 (and does not include nonlinear arithmetic operation unit 22), was taken as a comparative example, and a detection result at a time of measuring the same electrocardiogram waveform E as that in FIG. 10 was examined. FIG. 15 is graphs showing electrocardiogram waveform E measured by measurer 10, a time waveform I of a pulse sequence, which is obtained by filtering the electrocardiogram waveform E by linear processing unit 21, and a cardiac cycle (periodic signal) R_con detected by signal period detector 30.

The electrocardiogram waveform E and the time waveform of the pulse sequence in FIG. 15 are the same as the electrocardiogram waveform E and the input waveform I in FIG. 10.

Then, signal period detector 30 generates an amplitude envelope of the time waveform I of the pulse sequence, that is, an envelope of a peak level, and for example, sets 70% of the level as a threshold value. Then, the cardiac cycle R_con is detected by counting a time interval between points in each of which this threshold value and the pulse sequence I intersect each other; the points being adjacent to one another. The cardiac cycle R_con indicated by solid circles in FIG. 15 were detected. As shown in FIG. 15, the heartbeat cannot be detected correctly due to an influence of the noise N superimposed on the electrocardiogram waveform E, and a detection-disabled period occurs. In the detection-disabled period, signal period detector 30 cannot detect the cardiac cycle (solid circles) with respect to the cardiac cycle (blank circles) of the electrocardiogram waveform E.

A comparative examination is made between the cardiac cycle R_dev of FIG. 10 and the cardiac cycle R_con of the comparative example in FIG. 15. Signal detection device 1z of the comparative example employs the threshold value cross detection, and accordingly, causes "detection-disabled period" in the cardiac cycle R_con when the level fluctuation of the input waveform I is large. In a case where the level of the input waveform I is decreased, signal detection device 1z resets the threshold value for detecting the cardiac cycle. Specifically, the threshold value in the threshold value cross detection is updated to 70% of the peak level of the waveform each time. However, in a case where the level of the input waveform I is suddenly decreased, a signal level of the waveform sometimes fails down below the updated threshold value. In such a case, in order to reset an appropriate threshold value, a waiting period, which is a period equivalent to a few beats (for example, approximately 5 seconds), has been necessary. In the threshold value cross detection, normal detection cannot be performed in this waiting period, and accordingly, in signal detection device 1z, the detection-disabled period occurs when the level fluctuation of the input waveform I is large. In contrast, signal detection device 1 of the first exemplary embodiment adopts the zero-cross detection, and accordingly, the cardiac cycle R_dev, which is almost correct, can be detected without causing the detection-disabled period.

[Effects]

Signal detection device 1 of this exemplary embodiment includes: measurer 10; arithmetic operation unit 20; and signal period detector 30. Measurer 10 measures a signal. Arithmetic operation unit 20 performs nonlinear arithmetic operation processing for amplifying a pulse-like component of the signal measured by measurer 10, and suppressing a component other than the pulse-like component of the signal. Signal period detector 30 detects a periodic signal from an output of arithmetic operation unit 20. In this way, even in a case where an impedance between the signal detection device and a surface of a body fluctuates due to exercise such as body side flexion, a pulse-like signal such as a heartbeat waveform can be detected with high accuracy.

Note that, as described with reference to FIG. 3, if a DC component is mixed into the input variable IN, then it is possible that the output variable v may turn to a self-oscillation state. In signal detection device 1, linear processing unit 21 suppresses a low-frequency component including the DC component. In this way, the DC component is suppressed from being mixed into the input variable and nonlinear arithmetic operation unit 22 is prevented from falling into the self-oscillation state. However, when the subject is in rest or is doing light exercise, the DC component is less likely to be superimposed on the electrocardiogram waveform. In that case, the DC removal of linear processing unit 21 is omitted, and the nonlinear arithmetic operation by nonlinear arithmetic operation unit 22 is performed, whereby the pulse-like signal such as the heartbeat waveform can be detected with high accuracy.

Moreover, nonlinear arithmetic operation unit 22 of the present disclosure uses the resonating synchronization by using the FitzHugh-Nagumo equation. In this way, a high detection rate can be realized for the pulse-like signal having high periodicity.

Note that, in this exemplary embodiment, the signal detection device is defined to measure the heartbeat; however, may measure other pulse-like signals other than the heartbeat. Also in that case, noise can be removed, and the pulse-like signal desired to be measured can be detected with high accuracy.

Note that, in this exemplary embodiment, arithmetic operation unit 20 is defined to include linear processing unit 21 and nonlinear arithmetic operation unit 22; however, the arithmetic operation unit may perform the linear processing and the nonlinear arithmetic operation processing without distinguishing the linear processing unit and the nonlinear arithmetic operation unit. Moreover, only the nonlinear arithmetic operation processing may be performed.

Note that, in this exemplary embodiment, Expression 2 is derived from Expression 1 by the Euler method; however, other numerical solution (for example, Runge Kutta method) may be used.

The nonlinear arithmetic operation processing in the signal detection device and the signal detection method of this exemplary embodiment is arithmetically operated based on the input variable IN, the output variable $v_n$ and the intermediate variable $w_n$. The input variable IN corresponds to the input waveform I of the nonlinear arithmetic operation processing. The output variable $v_n$ corresponds to the output waveform F of the nonlinear arithmetic operation processing. As shown in Expression (2a), the variation of the output variable $v_n$ per time is arithmetically operated based on the intermediate variable $w_n$, the output variable $v_n$ and the input variable IN. As shown in Expression (2b), the variation of the intermediate variable $w_n$ per time is arithmetically operated based on the intermediate variable $w_n$ and the output variable $v_n$. Moreover, as shown in Expression (2c), an output variable $v_{n+1}$ corresponding to a certain point of time (defined as a first point of time) is arithmetically operated based on a product of the variation of the output variable $v_n$ per time and the time difference term $\Delta T$, and based on a value of an output variable $v_n$ at a past point of time (defined as a second point of time), which is past from the first point of time by the time difference term $\Delta T$. In this way, by the nonlinear arithmetic operation processing, the output waveform F is enabled to behave so as to resonate with the pulse component of the input waveform I.

Moreover, in accordance with the nonlinear arithmetic operation processing using the FN equation, even if the input variable IN is a constant value (first value), the output waveform F turns to the self-oscillation state, and a self-oscillation waveform that is a periodic waveform is output. Note that a range of values which can be taken as the first value described above depends on the respective constants of the FN equation. As shown in FIG. 3, when the input variable IN is a value (second value, 0 in FIG. 3) that does not stay within the range of the values where the input variable IN turns to the self-oscillation state, the output waveform F does not turn to the self-oscillation state. In this way, the FN equation can obtain such a stable amplification effect for the pulse component, and in addition, can suppress the noise other than the pulse component.

Moreover, in accordance with the nonlinear arithmetic operation processing using the FN equation, the repeating waveform including the pulse component is input to the input waveform I, whereby the output waveform F can be set to a resonance state. In this way, the output waveform F is output as a resonating signal waveform synchronized with the pulse component of the input waveform. In particular, in a case where the input waveform I is a waveform containing mainly a periodic pulse-like component, the output waveform F becomes a pulse waveform with the same cycle as that of the input waveform I. In this way; the first exemplary embodiment is effective for a case of detecting the period of the pulse from the input waveform I containing the pulse-like component.

Moreover, signal period detector 30 performs the zero-cross detection for detecting the point of time when the output waveform F intersects the predetermined detection threshold value, that is, 0. In this way, signal period detector 30 can detect the period stably without being affected by the amplitude of the output waveform F. Moreover, in accordance with the FN equation, the amplitude of the output waveform F can be stabilized. In this way, signal period detector 30 can detect the period more stably.

(Second Exemplary Embodiment)

Figure 16:
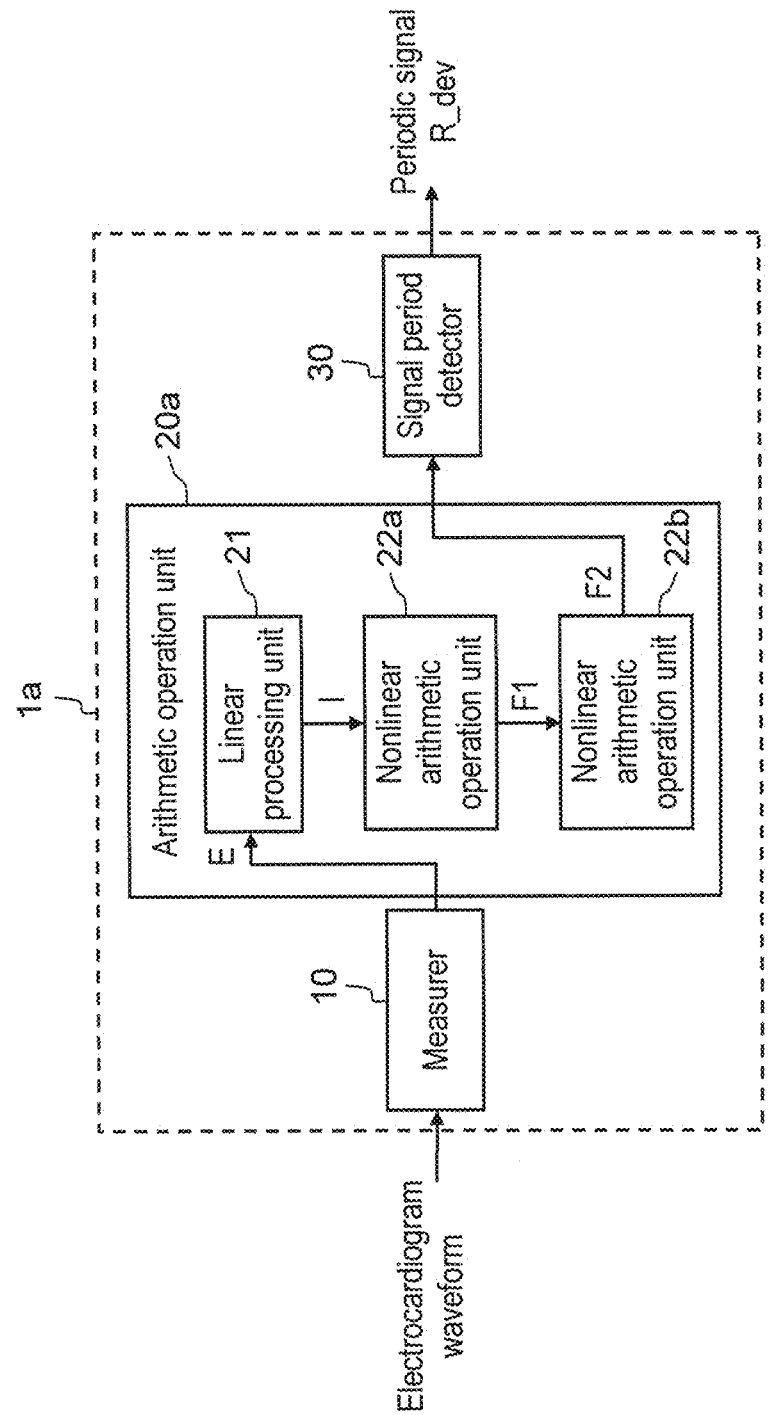
FIG. 16 is a block diagram showing a configuration of a signal detection device in a second exemplary embodiment.

FIG. 16 is a block diagram showing a configuration of signal detection device 1a according to a second exemplary embodiment. In signal detection device 1a, measurer 10 and signal period detector 30 are the same as those of the first exemplary embodiment, and arithmetic operation unit 20a is different from that of the first exemplary embodiment. Arithmetic operation unit 20a has a configuration of cascading linear processing unit 21 and two nonlinear arithmetic operation units 22a and 22b.

Hereinafter, functions/effects of cascading the nonlinear arithmetic operation units will be described.

[Regarding Cascading of Two Nonlinear Arithmetic Operation Units]

Figure 17:
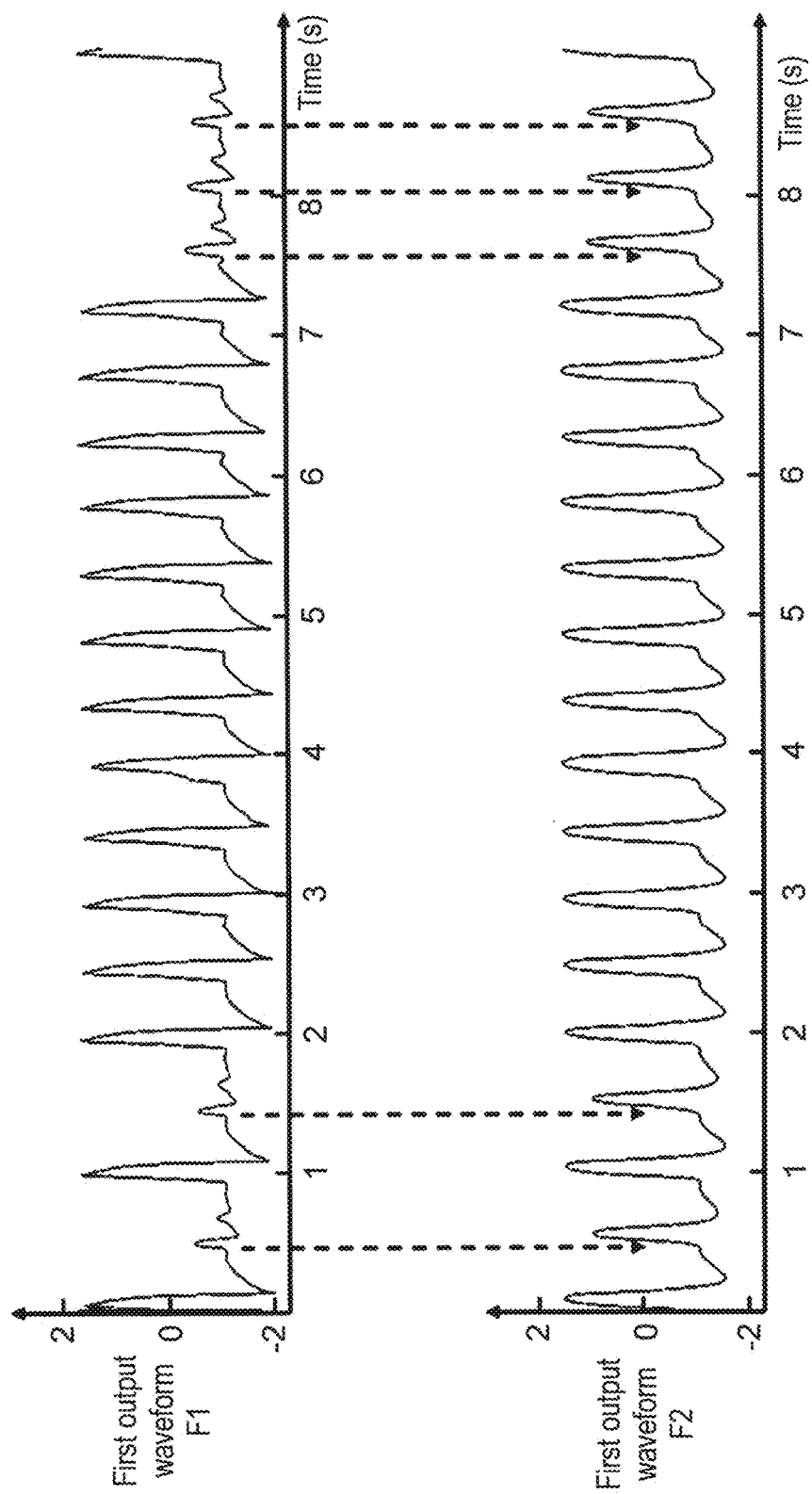
FIG. 17 is graphs in a case of inputting a heartbeat signal at a running time to an arithmetic operation unit of the second exemplary embodiment.

FIG. 17 is graphs showing behaviors of output waveforms at a time of cascading two nonlinear arithmetic operation units 22a and 22b, that is, inputting the output variable v of nonlinear arithmetic operation unit 22a to the input variable IN of nonlinear arithmetic operation unit 22b. An output variable of nonlinear arithmetic operation unit 22a is defined as a first output waveform F1, and an output variable of nonlinear arithmetic operation unit 22b is defined as a second output waveform F2. As shown by dotted-line arrows, imperfect resonances of nonlinear arithmetic operation unit 22a can be amplified by nonlinear arithmetic operation unit 22b. That is, arithmetic operation unit 20a performs the nonlinear arithmetic operation processing twice, and can thereby detect the pulse-like signal, which is desired to be measured, with high accuracy. Note that the pulse-like signal can be detected with higher accuracy by setting a number of cascaded nonlinear arithmetic operation units to a plural number that is three or more. Note that, for example, if the number of cascaded nonlinear arithmetic operation units is two, the second output waveform F2 corresponds to the output waveform F in the first exemplary embodiment. That is, signal period detector 30 generates the periodic signal based on the second output waveform F2.

The signal detection device and the signal detection method according to the present disclosure become capable of detecting the pulse-like signal such as a heartbeat waveform with high accuracy even in the case where the impedance between the signal detection device and the surface of the body fluctuates due to the exercise such as the body side flexion in a detection system of a biological signal such as the heartbeat waveform. Accordingly, the signal detection device and the signal detection method according to the present disclosure are useful for an exercise evaluation management system oriented for an individual or a fitness club.

What is claimed is:

1. A signal detection device comprising:
   a measurer that measures an electrocardiogram signal of a subject;
   an arithmetic operation unit that receives the electrocardiogram signal, performs nonlinear arithmetic operation processing on the electrocardiogram signal for amplifying a pulse-like component of the electrocardiogram signal and suppressing a component other than the pulse-like component of the electrocardiogram signals and outputs an output signal of the nonlinear arithmetic operation processing; and a signal period detector that detects a periodic signal and a frequency of the periodic signal from the output signal of the arithmetic operation unit, wherein:

the arithmetic operation unit selects a time difference term of the nonlinear arithmetic operation processing, based on the frequency of the periodic signal, and the arithmetic operation unit detects a cardiac cycle of the subject by performing the nonlinear arithmetic operation processing on the electrocardiogram signal with the selected time difference term;

wherein the nonlinear arithmetic operation processing is arithmetically operated based on an input variable corresponding to an input of the nonlinear arithmetic operation processing and based on an output variable corresponding to an output of the nonlinear arithmetic operation processing, when the input variable is constant at a first value, the output variable becomes a self-oscillation waveform, which is a periodic waveform, when the input variable is constant at a second value, the output variable becomes a constant value, when the input variable is a waveform mainly containing a periodic pulse-like component, the output variable becomes a resonating signal waveform, and a period of the resonating signal waveform is equal to a period of the waveform mainly containing the periodic pulse-like component.

2. The signal detection device according to claim 1, wherein
the arithmetic operation unit performs the nonlinear arithmetic operation processing after performing direct current (DC) removal for the electrocardiogram signal measured by the measurer.

3. The signal detection device according to claim 1, wherein the signal period detector detects the periodic signal by detecting a point of time when the resonating signal waveform intersects a predetermined detection threshold value.

4. The signal detection device according to claim 1, wherein
the arithmetic operation unit performs the nonlinear arithmetic operation processing a plurality of times.

5. The signal detection device according to claim 1, wherein
the nonlinear arithmetic operation processing is performed by using a FitzHugh-Nagumo equation.

6. The signal detection device according to claim 1, wherein
the nonlinear arithmetic operation processing is performed by a following expression:

$$v_n dot = c\left(-w_n + v_n - \frac{v_n^3}{3} + in\right)$$

$$w_n dot = v_n - bw_n + a$$

$$v_{n+1} = v_n + v_n dot \cdot \Delta T$$

$$w_{n+1} = w_n + w_n dot \cdot \Delta T$$

where in is an input variable corresponding to the electrocardiogram signal of the nonlinear arithmetic operation processing, vn is an output variable corresponding to the electrocardiogram signal of the nonlinear arithmetic operation processing, wn is an intermediate variable for the nonlinear arithmetic operation processing, $\Delta T$ is the time difference term, and a, b and c are predetermined constant terms.

7. The signal detection device according to claim 1, wherein
the periodic signal is a cycle of a heartbeat.

8. A signal detection method performed by a signal detection device, the signal detection method comprising:
measuring an electrocardiogram signal of a subject;
performing nonlinear arithmetic operation processing on the electrocardiogram signal for amplifying a pulse-like component of the electrocardiogram signal and suppressing a component other than the pulse-like component of the electrocardiogram signal and outputting an output signal of the nonlinear arithmetic operation processing;
detecting a periodic signal and a frequency of the periodic signal from the output signal of the nonlinear arithmetic operation processing;
setting selecting a time difference term of the nonlinear arithmetic operation processing, based on the frequency of the periodic signal; and
detecting a cardiac cycle of the subject by performing the nonlinear arithmetic operation processing with the selected time difference term;
wherein the nonlinear arithmetic operation processing is arithmetically operated based on an input variable corresponding to an input of the nonlinear arithmetic operation processing and based on an output variable corresponding to an output of the nonlinear arithmetic operation processing,
when the input variable is constant at a first value, the output variable becomes a self-oscillation waveform, which is a periodic waveform,
when the input variable is constant at a second value, the output variable becomes a constant value,
when the input variable is a waveform mainly containing a periodic pulse-like component, the output variable becomes a resonating signal waveform, and
a period of the resonating signal waveform is equal to a period of the waveform mainly containing the periodic pulse-like component.

9. The signal detection method according to claim 8, wherein
the electrocardiogram signal is subjected to direct current (DC) removal before the nonlinear arithmetic operation processing is performed.

10. The signal detection method according to claim 8, wherein:
the nonlinear arithmetic operation processing is arithmetically operated based on an input variable corresponding to an input of the nonlinear arithmetic operation processing and based on an output variable corresponding to an output of the nonlinear arithmetic operation processing,
when the input variable is constant at a first value, the output variable becomes a self-oscillation waveform, which is a periodic waveform,
when the input variable is constant at a second value, the output variable becomes a constant value,
when the input variable is a waveform mainly containing a periodic pulse-like component, the output variable becomes a resonating signal waveform, and a period of the resonating signal waveform is equal to the period of the waveform mainly containing the periodic pulse-like component.

11. The signal detection method according to claim 10, wherein
the periodic signal is detected by detecting a point of time when the resonating signal waveform intersects a predetermined detection threshold value.

12. The signal detection method according to claim 8, wherein
the nonlinear arithmetic operation processing is performed a plurality of times.

13. The signal detection method according to claim 8, wherein
the nonlinear arithmetic operation processing is performed by using a FitzHugh-Nagumo equation.

14. The signal detection method according to claim 8, wherein
the nonlinear arithmetic operation processing is performed by a following expression:

$$v_n dot = c\left(-w_n + v_n - \frac{v_n^3}{3} + in\right)$$

$$w_n dot = v_n - bw_n + a$$

$$v_{n+1} = v_n + v_n dot \cdot \Delta T$$

$$w_{n+1} = w_n + w_n dot \cdot \Delta T$$

where
in is an input variable corresponding to the electrocardiogram signal of the nonlinear arithmetic operation processing,
vn is an output variable corresponding to the electrocardiogram signal of the nonlinear arithmetic operation processing,
wn is an intermediate variable for the nonlinear arithmetic operation processing,
$\Delta T$ is the time difference term, and
a, b and c are predetermined constant terms.

15. The signal detection method according to claim 8, wherein
the periodic signal is a cycle of a heartbeat.

16. A method of detecting a cardiac cycle of a subject, the method comprising:
obtaining an electrocardiogram signal of the subject;
generating a first processed signal by performing nonlinear arithmetic operation processing on the electrocardiogram signal with an initial time difference term;
detecting a first periodic signal from the first processed signal and detecting a first frequency of the first periodic signal;
determining a new time difference term based on the first frequency; and
detecting the cardiac cycle of the subject by performing the nonlinear arithmetic operation processing on the electrocardiogram signal with the new time difference term;
wherein the nonlinear arithmetic operation processing is arithmetically operated based on an input variable corresponding to an input of the nonlinear arithmetic operation processing and based on an output variable corresponding to an output of the nonlinear arithmetic operation processing,
when the input variable is constant at a first value, the output variable becomes a self-oscillation waveform, which is a periodic waveform,
when the input variable is constant at a second value, the output variable becomes a constant value,
when the input variable is a waveform mainly containing a periodic pulse-like component, the output variable becomes a resonating signal waveform, and
a period of the resonating signal waveform is equal to a period of the waveform mainly containing the periodic pulse-like component.

17. The method according to claim 16, further comprising: generating a second processed signal by performing the nonlinear arithmetic operation processing on the electrocardiogram signal with the new time difference term;
detecting a second periodic signal from the second processed signal; and detecting a second frequency of the second periodic signal as the cardiac cycle of the subject.

18. The method according to claim 16, further comprising measuring the electrocardiogram signal of the subject.

19. The method according to claim 16, wherein renewal of the time difference term and performing the nonlinear arithmetic operation processing are repeated.

* * * * *